United States Patent [19]

Espey

[11] Patent Number: 5,356,876
[45] Date of Patent: Oct. 18, 1994

[54] METHODS OF TERMINATING PREGNANCY

[75] Inventor: Lawrence L. Espey, San Antonio, Tex.

[73] Assignee: Trinity university, San Antonio, Tex.

[21] Appl. No.: 933,981

[22] Filed: Aug. 21, 1992

Related U.S. Application Data

[63] Continuation-in-part of Ser. No. 819,830, Jan. 13, 1992, abandoned.

[51] Int. Cl.$^5$ .................. A61K 37/00; A61K 37/38; A61K 37/24
[52] U.S. Cl. ................................ 514/12; 514/21
[58] Field of Search ................... 514/12, 21

[56] References Cited

PUBLICATIONS

K. M. Doody and Carr, B. R. "Menstrual Cycle Disorders," Obstetrics and Gynocology of North America, vol. 17, No. 2, Jun. 1990.

Shohavu, Z. et al., "Early Miscarriage and Fetal . . . Intrafullopian Transfer," Fertility and Sterility, vol. 56 No. 2, Jan., 1990.

W. H. Yang and M. C. Chang "Interruption of Pregnancy . . . of PMS and hCG," Endocrundogy 83, pp. 217-224 1968.

Nakamura et al., "The pulsatile, subculareous administration . . . Nippon Sanka Fujinka", vol. 39, No. 12, pp. 2157-2164, 1987.

Gapo et al., "Menstrual Induction with Solproston" Prostaglandins, vol. 24, No. 5 pp. 657-665, 1982.

*Primary Examiner*—Lester L. Lee
*Assistant Examiner*—P. Lynn Touzeau
*Attorney, Agent, or Firm*—Cox & Smith Incorporated

[57] ABSTRACT

A method of terminating pregnancy in mammals is described by a novel application of the common fertility-promoting hormone known as human menopausal gonadotropin. A single injection of this gonadotropic hormone as early as the first day of conception can terminate pregnancy.

8 Claims, No Drawings

METHODS OF TERMINATING PREGNANCY

This application is a continuation-in-part of application Ser. No. 07/819,830 filed Jan. 13, 1992, now abandoned.

FIELD OF THE INVENTION

This invention relates to a novel use of the common fertility-promoting hormone hMG (human menopausal gonadotropin) as an agent to terminate the fertile state of pregnancy in female mammals. This invention also relates to the use of hMG for terminating pregnancies in humans.

BACKGROUND OF THE INVENTION

It is common scientific knowledge that fertility in mammals is the stage of life during which the ovaries and testes produce eggs and sperm, respectively. In the female gender this process involves the periodic development of ovarian follicles which contain the eggs. In the human species, for example, a pair of ovaries possesses an estimated 300,000 egg-bearing primordial follicles at the time of puberty. When an individual reaches sexual maturity, some of these follicles periodically develop and release their eggs (a phenomenon called ovulation). In all mammalian species that have been studied, the processes of follicular development and ovulation are regulated by two important hormones that are rhythmically secreted from the pituitary gland at the base of the brain. The active-hormones are follicle-stimulating hormone (FSH) and luteinizing hormone (LH). These two gonadotropic hormones are secreted by pituitary cells when the pituitary gland itself is stimulated by gonadotropin-releasing hormone (GnRH), a small peptide hormone that is produced by nerve cells in a portion of the forebrain known as the hypothalamus. Thus, mammalian fertility is controlled by both nervous and hormonal activities (Espey, L. L., and I. A. BenHalim, *Obstet. Gynecol. Clin. N. Amer.* 17:275, 1990)

FSH and LH are large glycoprotein molecules that belong to a group of hormones collectively referred to as "gonadotropins" because they stimulate the gonads. When one or more ovarian follicles reaches maturity by the actions of these hormones, there is a surge in GnRH secretion from the hypothalamus, and this surge promotes a sharp increase in FSH and LH release from the pituitary gland. This sudden increase in gonadotropins stimulates the mature ovarian follicles to enter what is called the "ovulatory process". The ovulatory process requires approximately 10 to 40 hours, depending on the species of mammal. At the end of this metabolic process, the mature ovarian follicles rupture and release fertile eggs into the oviduct (Espey, L. L., and I. A. BenHalim, *Obstet. Gynecol. Clin. N. Amer,* 17:275, 1990)

If an egg is fertilized and the developing embryo becomes implanted in the uterus, special embryonic cells called trophoblasts begin secreting a hormone called chorionic gonadotropin (CG). (In humans this hormone is called human chorionic gonadotropin and is abbreviated as hCG.) CG circulates from the uterus back to the ovaries and stimulates any ruptured follicles (which are now called corpora lutea) to produce large amounts of the steroid hormone progesterone (Espey, L. L., and I. A. BenHalim, *Obstet. Gynecol. Clin. N. Amer.* 17:275, 1990).

Progesterone has two principal functions; (1) it maintains the uterine lining in the nutritive state that is required to support a developing embryo, and (2) it circulates back to the hypothalamus and the pituitary gland and inhibits further secretion of GnRH, FSH, and LH. This inhibitory action of progesterone prevents a second ovulatory process from occurring in a gravid animal. That is to say, a second pregnancy cannot occur "on top of" an existing pregnancy. Thus, progesterone functions as a natural contraceptive during pregnancy. This steroid hormone is also the basis of the oral contraceptive pills that are commonly used today. Synthetic progestins (along with some estrogens) are used in "the pill" to block ovulation by inhibiting the normal pre-ovulatory surge in GnRH, FSH, and LH (Espey, L. L., and I. A. BenHalim, *Obstet. Gynecol. Clin. N. Amer.* 17:275, 1990).

At the time of menopause, the ovaries lose their capacity to produce significant amounts of progesterone and other sex steroids like estradiol. The reduction in these ovarian steroid hormones causes an abatement in the negative feedback action that they normally have on the hypothalamus and the pituitary gland. The rest-fit of this decline in inhibitory action is a significant increase in the secretion of FSH and LH from the pituitary glands of menopausal women. These two "menopausal gonadotropins" (i.e., FSH and LH) are filtered by the kidneys from the blood into the urine. Thus, human menopausal gonadotropin (hMG) is a urinary extract that contains substantial amounts of both FSH and LH, two gonadotropic hormones with similar origins and similar molecular configurations. Since menopausal urine contains a high concentration of hMG, extracts of human urine are the most common source of commercial preparations of hMG that are used to induce ovulation and fertility in women (Harlin, J., S. A. Khan, and E. Diczfalusy, *Fertil. Steril.* 46:1005, 1986; Cook, A. S., B. W. Webster, P. F. Terranova, and B. A. Keel, *Fertil. Steril.* 49:704, 1988; Corsan, G. H., and E. Kemmann, *Fertil. Steril.* 55:468, 1991).

SUMMARY OF THE INVENTION

This invention relates to a method of terminating pregnancy in mammals by the administration of hMG, or equivalent hormone preparations. The novelty of this invention is that hMG has been used heretofore to induce ovulation and fertility in non-pregnant women. This invention reveals that a single injection of hMG can also induce follicular maturation and ovulation in pregnant laboratory animals. Such treatment has an abortifacient effect and terminates the gravid state of the animals.

DESCRIPTION OF THE INVENTION

Human menopausal gonadotropin (hMG) (also called menotropin) is commonly used to treat infertility in women (Corsan, G. H., and E. Kemmann, *Fertil. Steril.* 55:468, 1991; Gougeon, A., and J. Testart, *Fertil. Steril.* 54:848, 1990). This extract from menopausal urine has both follicle-stimulating hormone (FSH) and luteinizing hormone (LH) activities. Therefore, hMG can induce ovarian follicular maturation and cause ovulation. While this fertility-promoting action of hMG is well known, there is negligible information about the effect of this hormone on pregnant individuals. This invention teaches that hMG can also induce follicular maturation and ovulation in pregnant animals. The supporting experiments show that a single dose of hMG can stimulate ovarian follicular development and ovulation when it is injected subcutaneously into pregnant laboratory rats. The experiments also assess the effect of these hMG-induced events on the gravid state of the experimental animals. The results show that hMG will terminate an existing pregnancy when the hormone is administered during the first one-third of the gestation period.

The hMG utilized in the experimental section of this patent was purchased from Sigma Chemical Company (St. Louis, Mo.). As stated above, hMG is a urinary extract from menopausal women that contains both FSH and LH activities. Other commercial sources for these hormones also exist, as well as methods for their purification from natural sources by chemical and recombinant technology. The hormone amounts may be, in general, expressed in international units (I.U.), or by weight. These units are described in The United States Pharmacopeia, as revised and published by the Board of Trustees of the United States Pharmacopeial Convention, Inc., on Jan. 1, 1990. Typically, a single milligram of hMG supplied by Sigma Chemical Company contains approximately 50 I.U. of FSH activity and 50 I.U. of LH activity.

Wistar laboratory rats for the experiments were selected from a breeding colony on the basis of their age and weight. When the young females reached approximately 55 days of age, vaginal smears were performed each morning to confirm sexual maturity of the animals and to monitor their sexual cycles. Mature rats weighing 180–220 grams were caged with adult males for 24 hours beginning at noon on the day of proestrus. At the end of this 24-hour period, a final vaginal smear was performed to confirm that the animals were in estrus and that sperm were present in their vaginal tracts. This simple routine is a reliable method of establishing the first day of pregnancy.

EXAMPLE 1

In the first experiment, three groups of pregnant rats were used to assess whether hMG could induce follicular development and ovulation during pregnancy (TABLE 1):

TABLE 1

Gonadotropin-induced ovulation rate in pregnant rats

| GROUP | DOSE | OVULATION RATE (ova/rat) | | | | | MEAN |
|---|---|---|---|---|---|---|---|
| CONTROL | | 0 | 0 | 0 | 0 | 0 | 0 |
| hMG Day-6 | 0.5 mg/rat | 3 | 0 | 0 | 0 | 5 | 1.6 + 1.2 |
| hMG Day-6 ± hCG | 0.5 mg/rat 50 IU/ | 22 | 19 | 13 | 13 | 9 | 15.0 + 2.8 |
| Day-8 | rat | | | | | | |

The control group was not treated with any hormones. The two experimental groups were injected subcutaneously with 0.5 mg hMG (Sigma Chemical Company product G-8760) in 0.5 ml distilled water on Day-6 of pregnancy. The latter experimental group was treated subsequently 2 days later with human chorionic gonadotropin (hCG), a common substitute for LH to induce ovulation. The hCG (Sigma Chemical Company product CG-5) was injected subcutaneously in a single dose of 50 I.U. in 0.5 ml distilled water. Twenty-four hours later (i.e., on Day-9 of pregnancy) the oviducts were removed from all of the animals in the three groups, and the number of ova in the oviducts were counted in order to tabulate the ovulation rates. The results in TABLE 1 show that there were no ovulations in the control animals, a mean ovulation rate of $1.6 \pm 1.2$ ova/rat in the hMG-treated animals, and a mean ovulation rate of $15.0 \pm 2.8$ ova/rat in the hMG/hCG-treated animals. Statistical analysis of the data by the t-test for the difference between two independent means confirms that the mean values of both experimental groups were significantly different ($p < 0.05$) from the control group. Thus, the data show that follicles which develop in pregnant animals in response to hMG treatment have the ability to ovulate. Also, the data show that exogenous hCG significantly enhances the ovulation rate of such follicles. The pregnant state of all the animals was confirmed by counting the number of fetuses in the uteri at the time the oviducts were removed to tabulate ovulation rates. There were $11.4 \pm 1.6$ fetuses in the control group, $10.8 \pm 1.1$ fetuses in the hMG-treated group, and $11.2 \pm 0.7$ fetuses in the hMG/hCG-treated group. These values are all in the range of the normal litter size of an adult rat.

EXAMPLE 2

In the second experiment, nine groups of pregnant rats were used to assess the effects of hMG on pregnancy (TABLE 2):

TABLE 2

Termination of pregnancy by treatment with hMG

| GROUP | DOSE | LITTER SIZES (per rat) | | | | | | | | MEAN |
|---|---|---|---|---|---|---|---|---|---|---|
| CONTROL | — | 15, | 15, | 13, | 17, | 8, | 6, | 8, | 11 | 11.8 + 1.3 |
| hMG/DAY-1 | 0.5 mg/rat | 0 | 0 | 0 | 0 | | | | 0 | 0 |
| bMG/DAY-2 | 0.5 mg/rat | 0 | 0 | 0 | 0 | | | | 0 | 0 |
| hMG/DAY-3 | 0.5 mg/rat | 0 | 5 | 0 | 0 | | | | 10 | 3.0 + 2.00 |
| hMG/DAY-3,4 | 0.5 mg/rat | 0 | 0 | 0 | 0 | | | | 0 | 0 |
| hMG/DAY-6 | 0.5 mg/rat | 2 | 5 | 9 | 1 | | | | 13 | 6.0 + 2.2 |
| hMG/DAY-6,7 | 0.5 mg/rat | 0 | 0 | 7 | 11 | | | | died | 4.5 + 2.7 |
| hMG/DAY-6 | 1.0 mg/rat | 0 | 0 | 0 | 0 | | | | 2* | 0 |
| hMG/DAY-6 + hMG/DAY-8 | 0.5 mg/rat 50 IU/rat | 0 | 0 | 0 | 3 | | | | 5* | 0.6 + 0.6 |

In this study, the effect of hMG on litter size was determined after the hormone was administered (1) on different days of the gestation period, (2) in multiple doses, (3) in different amounts, and (4) in conjunction with hCG. Day-1 of pregnancy is defined as the day of estrus during which the female mated with a male rat. The data show that hMG terminated pregnancy in all of the rats when 0.5 mg of the hormone were injected in a single dose on either Day-1 or Day-2 of gestation.

Pregnancy was also terminated when a double dose of 0.5 mg hMG was administered to the animals on both Day-3 and Day-4 of pregnancy. In addition, the mean number of animals in the litters were statistically lower ($p < 0.05$) than the control value of $11.8 \pm 1.3$ when the pregnant animals were (1) treated with 0.5 mg hMG/rat on Day-3 or Day-6, (2) treated with 0.5 mg hMG/rat on Days-6,7, (3) treated with 1.0 mg hMG/rat on Day-6, or (4) treated with 0.5 mg hMG/rat on Day-6 followed by 50 I.U. hCG/rat on Day-8. When hMG was given on both days 6 and 7, one of the animals died. This event was associated with excessive vaginal bleeding. Also, in two instances (see asterisks in TABLE 2), the litters were stillborn several days after the normal parturition date.

The data in EXAMPLE 2 show that a single dose of 0.5 mg hMG/rat is more effective ($p < 0.05$) in terminating pregnancy when the hormone preparation is administered on Day-1 or Day-2 of pregnancy compared to an equivalent injection on Day-3 or Day-6. This information demonstrates that the method is more efficient when it is administered during the earlier stages of gestation. Nevertheless, the data show that pregnancy can also be terminated by hMG when the hormone is administered as late as 6 to 7 days after conception. Therefore, since the normal gestation period in the rat is 21 to 22 days, the data in EXAMPLE 2 demonstrate that hMG can be administered at least during the first one-third of the gestation period, and preferably during the first one-tenth of gestation. In comparison, in the 266-day gestation period of a human being, the equivalent intervals would be during the first trimester, and preferably during the first four weeks of gestation, respectively.

The data in EXAMPLE 2 also show that the efficiency of pregnancy termination was significantly greater ($p < 0.05$) when hCG was injected on Day-8 (i.e., on the second day after treatment with hMG) compared to when no hCG was administered. In comparison, the data in EXAMPLE 1 show that the frequency of ovulation is significantly greater ($p < 0.05$) when hCG was injected on Day-8, 2 days after the hMG treatment. Therefore, taken together, EXAMPLES 1 and 2 reveal a correlation between the induction of ovulation in the pregnant animals and the frequency of pregnancy termination following hormonal treatment. That is to say, a hormonal regimen that induces ovulation in a pregnant mammal is more likely to terminate the gravid state of the animal.

Since urinary extracts of hMG consist of both FSH and LH (Stone, B. A., K. Quinn, P. Quinn, J. M. Vargyas, and R. P. Marts, *Fertil. Steril.* 52:745, 1989; Harlin, J., S. A. Khan, and E. Diczfalusy, *Fertil. Steril.* 46:1005, 1986) the abortifacient action of this hormonal extract is based on the combined effects of these two pituitary hormones. The ratio of FSH and LH in different hMG preparations is dependent in part on the extraction procedures that are used to obtain the hormone from urine samples (Harlin, J., S. A. Khan, and E. Diczfalusy, *Fertil. Steril.* 46:1005, 1986; Cook, A. S., B. W. Webster, P. F. Terranova, and B. A. Keel, *Fertil. Steril.* 49:704, 1988; Corsan, G. H., and E. Kemmann, *Fertil. Steril.* 55:468, 1991). The FSH and LH activities in such preparations of hMG are biologically standardized in terms of the Second International Reference Preparation for Human Menopausal Gonadotropins established in September, 1964, by the Expert Committee on Biological Standards of the World Health Organization (*Physicians' Desk Reference,* 46th Edition, published by Medical Economics Data, Oradell, N.J., 1992, p. 2184). In the commercial preparations used in the experiments described in EXAMPLES 1 and 2 above, 1.0 mg hMG contained approximately 50 I.U. each of FSH and LH activities. Therefore, treatment of a 250 g rat with 0.5 mg hMG amounts to a dose of 2.0 mg hMG/kg rat weight, which is equivalent to approximately 100 I.U. each of FSH and LH per kg of body weight (with hMG preparations from Sigma Chemical Company). However, the dosage of hMG (and hCG) that would be adequate to terminate pregnancy in a human being has not yet been confirmed by actual tests. In fact, there is negligible information about the effects of hMG when it is administered to a pregnant human being (*Physicians' Desk Reference,* 46th Edition, published by Medical Economics Data, Oradell, N.J., 1992, p. 2184).

As stated above, the data in EXAMPLES 1 and 2 indicate that the efficiency of pregnancy-termination is greater when the regimen of gonadotropin treatment induces ovulation in the treated animal. Therefore, the amount of hMG (and hCG) that would be required to terminate pregnancy in a human being would probably be equivalent to an amount that is adequate to induce ovulation. In a non-pregnant, infertile human being, ovulation can be induced by a variety of hormonal regimens which utilize one or more common commercial sources of hMG, FSH, LH, and/or hCG (Gougeon, A., and J. Testart, *Fertil. Steril.* 54:848, 1990; Dodson, W. C., C. L. Hughes, Jr., and A. F. Haney, *Am. J. Obstet. Gynecol.* 159:382, 1988; Martinez, A. R., R. E. Bernardus, F. J. Voorhorst, J. P. W. Vermeiden, and J. Schoemaker, *Fertil. Steril.* 55:258, 1991; Chaffkin, L. M., J. C. Nulsen, A. A. Luciano, and D. A. Metzger, *Fertil. Steril.* 55:252, 1991; Stone, B. A., K. Quinn, P. Quinn, J. M Vargyas, and R. P. Marrs, *Fertil. Steril.* 52:745, 1989; Harlin, J., S. A. Khan, and E. Diczfalusy, *Fertil. Steril.* 46:1005, 1986; Tanbo, T., P. O. Dale, E. Kjekshus, E. Haug, and T. Abyholm, *Fertil. Steril.* 53:798, 1990; Anderson, R. E., J. M. Cragun, R. J. Chang, F. Z. Stanczyk, and R. A. Lobo, *Fertil. Steril.* 52:216, 1989). It is reasonable to expect any of the protocols that induce follicular maturation and ovulation in infertile women to represent approximately the same hormone dosages that would be required to induce follicular maturation and ovulation and cause an abortion in a pregnant woman. In brief, the more common protocols for inducing ovulation in infertile women consist of individual daily doses of hMG (comprising about 75 to 300 I.U. each of FSH and LH activities) for about seven consecutive days, beginning 3 to 5 days after the start of any one menstrual cycle. Also, hormonal preparations that consist mainly of FSH can be substituted for hMG in the above protocols (Gemzell, C. A., E. Diczfalusy, and G. Tillinger, *J. Clin. Endocr. Metab.* 18:1333, 1958; Tanbo, T., P. O. Dale, E. Kjekshus, E. Haug, and T. Abyholm, *Fertil. Steril.* 53:798, 1990; Anderson, R. E., J. M. Cragun, R. J. Chang, F. Z. Stanczyk, and R. A. Lobo, *Fertil. Steril.* 52:216, 1989). The last daily dosage of hMG (or FSH) is normally followed 24 to 48 hours later by an ovulation-inducing dose of hCG, amounting to about 5,000 to 10,000 I.U. of hCG. It is reasonable to expect these same protocols to induce follicular maturation and ovulation in pregnant human beings and to thereby cause termination of the gravid state.

In the above examples, it is scientifically reasonable to expect the same biological responses if LH is used as a substitute for hCG, or vice versa. Such a substitution is possible because it is common knowledge that LH and hCG are members of the same family of hormones. Both LH and hCG are heterodimeric glycoproteins composed of a common α-subunit and a closely related β-subunit. The similarity in these molecular configurations allows both hormones to bind to the same membrane receptors on the surface of target cells in the body, and therefore LH and hCG elicit identical biological responses (Roche, P. C., and R. J. Ryan, *J. Biol. Chem.* 264:4636, 1989; McFarland, K. C., R. Sprengel, H. S. Phillips, M. Kohler, N. Rosemblit, K. Nikolics, D. L. Segaloff, and P. H. Seeburg, *Science* 245:494, 1989).

It is common scientific knowledge that most hormones have similar functions in all vertebrate animals (Biology, 3rd Edition, by P. H. Raven and G. B. Johnson, published by Mosby Year Book, Inc., St. Louis, Mo., 1992, p. 965). In the class of vertebrates known as mammals, it is even more likely that common hormones such as the gonadotropins each have the same specific functions in different species of mammals. Therefore, it is reasonable to expect the abortifacient action of the gonadotropic hormones described in EXAMPLES 1 and 2 above involving laboratory rats to also be applicable to other mammalian species. Comparable abortifacient action in human beings is especially feasible, in view of the fact that the hMG and hCG preparations that were used in the experiments described in EXAMPLES 1 and 2 above were, by definition, hormones of human origin.

Although the hormones in EXAMPLES 1 and 2 above were dissolved in distilled water, it is scientifically reasonable to expect them to exert the same abortifacient action if they are dissolved and administered in other pharmacologically inert solutions such as physiological salines and/or physiological buffers. Also, although the hormones were administered via subcutaneous injections, it is equally reasonable to expect them to exert the same abortifacient action if they are administered intramuscularly, intravenously, or by any other route that does not alter the normal molecular composition of the hormones.

The pregnancy-terminating action of hMG (and hCG) is different from that of the abortifacient agent RU486. RU486 (also called mifeprestone) is a synthetic steroid that blocks target cell receptors for progesterone and thereby terminates pregnancy (Baulieu, E. E., *Endocrinology* 127:2043, 1990). During the past decade, this progesterone antagonist has been used more and more extensively as an abortifacient agent (Silvestre, L., C. Dubois, M. Renault, Y. Rezvani, E. E. Baulieu, and A. Ulmann, *New Engl. J. Med.* 322:645, 1990). RU486 also reportedly inhibits ovulation and the formation of corpora lutea (Baulieu, E. E., *Endocrinology* 127:2043, 1990). Thus, the mechanism of action of this agent is quite different from that of hMG, even though both compounds share the ability to terminate pregnancy. Also, in regard to RU486, it is well known that analogs of prostaglandin E increase the pregnancy-terminating ability of this drug from about 80% effectiveness to about 96% (Baulieu, E. E., *Endocrinology* 127:2043, 1990; Silvestre, L., C. Dubois, M. Renault, Y. Rezvani, E. E. Baulieu, and A. Ulmann, *New Engl. J. Med.* 322:645,1990). The enhancing action of prostaglandin E is based on the ability of this substance to induce muscle contractions in the myometrial tissue of the uterus. This observation makes it scientifically reasonable to expect the abortifacient action of hMG to be enhanced by concomitant treatment of pregnant animals with hMG (and hCG) and prostaglandin E. For example, on the basis of existing knowledge about enhancement of the abortifacient action of RU486 in humans by supplementary treatment -with prostanoids, prostaglandin $E_2$ (or an equivalent analog) would be administered either as a vaginal suppository containing about 0.5 to 1.0 mg of the active prostaglandin, or as an intramuscular injection consisting of a total of 0.125 to 0.5 mg of the active prostaglandin, at approximately 24 to 48 hours after administration of the final daily dose of hMG, or after the single dose of hCG when this latter gonadotropin is given in conjunction with hMG (Silvestre, L., C. Dubois, M. Renault, Y. Rezvani, E. E. Baulieu, and A. Ulmann, *New Engl. J. Med.* 322:645,1990; Guillebaud, J., *Brit. Med. J.* 30 1:352, 1990).

In summary, the invention is a method of terminating pregnancy by the administration of single or multiple doses of hMG to induce ovarian follicular maturation and ovulation during the first one-third of the gestation period of any given species of mammal. Since hMG is a human urinary extract that contains both FSH and LH as the two active ingredients, it is reasonable to expect combinations of FSH and LH to exert the same abortifacient action as hMG. It is also reasonable to expect the abortifacient action of hMG (and/or FSH and LH) to be enhanced when such hormone preparations are administered in conjunction with hCG or prostaglandin $E_2$, as described above. Since hMG and hCG are hormones of human origin, the method should be particularly effective in human beings. The novelty of this invention is that the described protocols have been used heretofore as methods of inducing fertility in non-pregnant women, rather than as pregnancy-terminating procedures.

I claim:

1. A method of terminating pregnancy in a mammal by inducing ovarian follicular maturation and ovulation during the period from the first day of conception to the end of the first trimester of the normal gestation period for the mammal, the method comprising:

injecting into the mammal a dosage of fertility promoting hormones selected from the group consisting of hMG, and the combination of FSH and LH, wherein the fertility promoting hormones are injected for up to seven consecutive days and wherein the fertility promoting hormones have a FSH activity of from seventy-five to three hundred I.U. and an LH activity of from seventy-five to three hundred I.U.

2. The method of claim 1 wherein said injection is administered subcutaneously.

3. The method of claim 1 wherein said injection is administered intramuscularly.

4. The method of claim 1 wherein said injection is administered intravenously.

5. The method of claim 1 wherein said dosage comprises substantially equal quantities of FSH and LH.

6. The method of claim 1 wherein the mammal is a woman.

7. The method of claim 1 further comprising injecting an ovulation inducing dosage of hCG in the range of 5,000 to 10,000 I.U. 24 to 48 hours after the last injection of the fertility promoting hormone.

8. The method of claim 1 further comprising administering to the mammal prostaglandin E in an amount of from 75 to 150 I.U./kg of body weight substantially concurrently with the last injection of said fertility promoting hormone.

* * * * *